(12) United States Patent
Zonenshayn

(10) Patent No.: US 6,301,492 B1
(45) Date of Patent: Oct. 9, 2001

(54) DEVICE FOR PERFORMING MICROELECTRODE RECORDINGS THROUGH THE CENTRAL CHANNEL OF A DEEP-BRAIN STIMULATION ELECTRODE

(75) Inventor: Martin Zonenshayn, New York City, NY (US)

(73) Assignee: ElectroCore Technologies, LLC, Summit, NJ (US)

( * ) Notice: Subject to any disclaimer, the term of this patent is extended or adjusted under 35 U.S.C. 154(b) by 0 days.

(21) Appl. No.: 09/489,001

(22) Filed: Jan. 20, 2000

(51) Int. Cl.[7] ........................................... A61B 5/05
(52) U.S. Cl. ........................................... 600/378
(58) Field of Search ........................... 600/372, 373, 600/378, 544

Primary Examiner—William E. Kamm

(74) Attorney, Agent, or Firm—Joseph P. Errico, Esq.; Timothy J. Bortree, Esq.

(57) ABSTRACT

A combined deep brain stimulation electrode and microelectrode recording probe are provided to reduce the tedium and difficulty associated with the localization of electrical stimulation leads, thereby promoting neurosurgeons to use the most sophisticated methods of electrode placement. The invention includes a deep brain stimulator having an elongate elastomeric sheath which encases a series of individually wound wires extending from one end of the electrode to the other, and terminating in a corresponding series of electrically isolated contact pads. The interior of the elongate sheath is a central channel which is open at both ends. The microelectrode probe is advanced through the central channel and provides one pole of an electrical stimulator tip. One of the deep brain stimulator contact pads serves as the other pole for the microelectrode recording process. Once the proper position is determined, the deep brain stimulator maybe advanced into position, and the microelectrode recording probe may be removed.

5 Claims, 1 Drawing Sheet

DEVICE FOR PERFORMING MICROELECTRODE RECORDINGS THROUGH THE CENTRAL CHANNEL OF A DEEP-BRAIN STIMULATION ELECTRODE

BACKGROUND OF INVENTION

1. Field of Invention

The present invention pertains to an assembly for facilitating microelectrode recordings in the brain during implantation of deep brain stimulation hardware.

2. Description of Prior Art

The use of chronic electrical stimulation in the treatment of a variety of neurological disorders, including, but not limited to, Parkinson's disease, dystonia, essential tremor, and chronic pain, has recently revolutionized the field of functional neurosurgery. New applications of this technology are being forecast by experts in the field at a rapid rate, and many applications have indeed already been envisioned. These new applications encompass many diverse neurological disorders, such as obsessive-compulsive disorder, obesity, anorexia, tinnitus, dyslexia, and many others. The efforts to control some of these illnesses are finally coming to fruition.

The surgery for afflictions most commonly being treated by functional neurosurgeons today, namely Parkinson's disease, essential tremor, and chronic pain, demands a high degree of spatial precision. These treatments require the targeting of different areas within the brain to produce positive outcomes. It has been recognized, and increasingly accepted, that chronic deep-brain stimulation holds several advantages over alternative methods of surgical treatment, namely lesioning, inasmuch as lesioning can only permanently destroy neuronal activity. In most instances, the preferred effect is to stimulate or reversibly block activity in nervous tissue. Electrical stimulation is reversible and adjustable, by modification of such electrical parameters as frequency, pulse width, and amplitude of the electrical current.

There are several methods currently available, both invasive and non-invasive, for targeting deep brain structures. The non-invasive methods generally rely on imaging technologies, such as computer tomography, magnetic resonance, or positron emission tomographic imaging. Each method has its advantages and disadvantages. The most ideal method would enable the visualization of the structure of interest at a high degree of spatial accuracy. The best commercially-available technique currently provides an accuracy greater than a millimeter. The invasive methods, which include micro- or semi-microelectrode recording, and macrostimulation, however, can optimally yield submillimeter precision. Specifically, microelectrode recording can be used to record individual cell characteristics at a spatial interval of a micron. Macroelectrode stimulation, on the other hand, activates or inhibits hundreds to thousands of cells at a time. As precision in locating the stimulation is most important component of success, most experienced medical centers performing these types of surgery utilize the technique of microelectrode recording (MER), in addition to other methods, to gain sub-millimeter spatial accuracy during the implantation of deep brain stimulating electrodes. Unfortunately, because of the time commitment and expense associated with using independent microelectrode recording (MER) systems the majority of neurosurgeons worldwide who are performing deep-brain stimulation procedures do not use the technique. They generally rely on only non-invasive neuroimaging (usually magnetic resonance imaging) as an initial targeting method, and then solely on macrostimulation to refine the final position of the permanent electrode. The potential lack of precision in locating the electrode is the most important predictor of a good surgical outcome, results may not be as optimal as those obtained by including MER in the targeting armamentarium.

In particular, the assembly and process for microelectrode recording comprises a passing a 1.1 mm microelectrode carrier tube to a predefined distance above the MRI-defined target within the brain, typically 15 mm above target, and performing MER via a microelectrode housed within the hollow center of the carrier tube. The typical microelectrode consists of a stainless steel wire, approximately 0.27 mm in diameter, with an insulating polyamide coating. Typically, it has an attached tungsten tip with a diameter of 1–3 $\mu$m, and an impedance of 500 to 1000 kOhms at a typical frequency of 1000 Hz. This, in turn, is housed in a stainless steel carrier tube with an external insulating teflon coat and a total outer diameter of 1.1 mm. The microelectrode tip is used as one pole of an electrical circuit, and the distal exposed portion of the stainless steel carrier tube is used as the other pole to form a current loop. Cycling through the steps of microstimulation, recording, analyzing the results, and, if necessary, advancing of the lead to a new location is carried out until the specific ideal location is identified. While this provides the best localization of the deep brain stimulationlead, as suggested above, there are several technical reasons why many neurosurgeons do not routinely employ MER during the placement of deep-brain electrodes. First, recordings may take anywhere from 1 to 10 or more hours to perform. Second, the use of the microelectrode requires additional electronic equipment and the aid of a neurophysiologist. Third, there are some who believe that multiple microelectrode insertions and movements into and within thee brain may increase the complication rate of the surgery. While the tip of the microelectrode is only 1–3 microns in diameter, the carrier tube that houses the electrode is 1.1 mm in diameter, which is not an insignificant thickness considering that the size of a typical neuron is several magnitudes smaller. As such, most practicing functional neurosurgeons do not perform MER routinely believing that its possible risks outweigh its benefits.

SUMMARY OF THE INVENTION

The object of the present invention is to combine microelectrode recording leads (MER leads) with the ultimate deep brain stimulation (DBS) electrode placement into a single step, thereby minimizing complications. It is a further object of this invention to facilitate the use of microelectrode recordings (MERs) and make it more accessible to functional neurosurgeons.

These and other objects are met by the present invention which is a device which provides a microelectrode recording (MER) lead mounted within the central axial channel of a deep brain stimulation lead. More particularly, the standard deep brain stimulation electrode comprises an elongate elastomeric sheath having a plurality of independently helically wound wires disposed therein. The wires terminate at opposing ends of the electrode at electrical contact pads. The central axis of the electrode structure is a channel in which a semi-rigid stylet is removeably mounted. The stylet is provided to supply a modicum of stiffness to the structure during implantation, only to be removed after final positioning. In fact, the electrode is implanted through a cannula which is inserted into the brain. The stylet is advantageous to advancing the lead through the cannula, but is somewhat superfluous as the cannula is rigid and provides ample stiffness for effective positioning. The present invention takes advantage of this by mounting the microelectrode recording (MER) lead in the stylet channel, relying on the cannula to provide the requisite rigidity.

DETAILED DESCRIPTION OF THE PREFERRED EMBODIMENT

Figure 1:
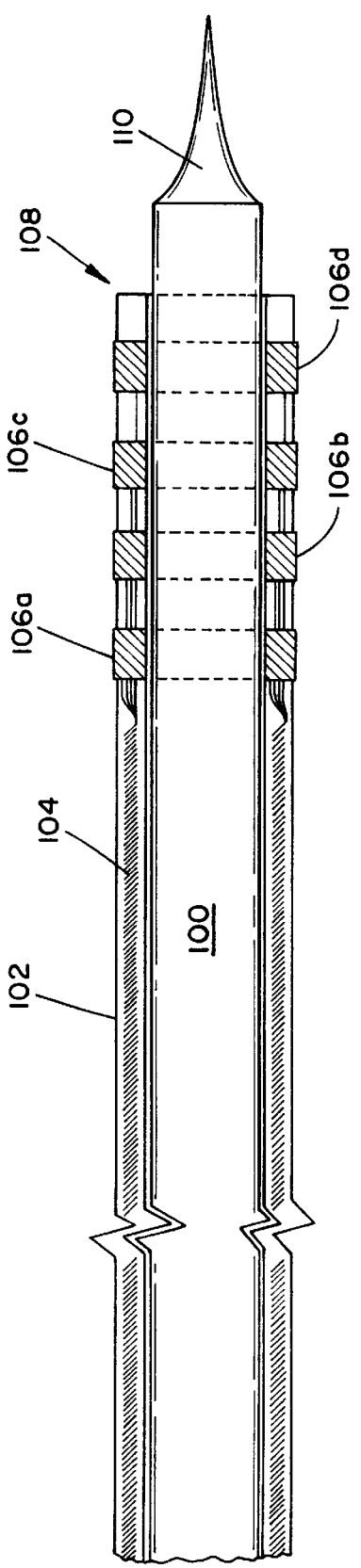
FIG. 1 comprises a side cross section view of the microelectrode recorder and deep brain stimulation assembly of the present invention.

The present invention combines microelectrode recording (MER) with the final deep brain stimulation lead placement into a single step, thereby facilitating microelectrode recording (MER) and more precision in deep brain stimulation lead placement. For the purposes of this description and appended claims, the term "lead" is used herein in its broadest sense and includes a stimulation lead, a sensing lead, a combination thereof, or any other elongated member, such as a catheter, which may be usefully passed to its target within the brain.

The present invention provides a means for performing microelectrode recording (MER) via the same lead which is normally implanted at the conclusion of the functional neurosurgical procedure. This final lead is implanted within a specific brain structure at a location which is deemed appropriate for the particular medical condition. As described above, in the Summary of the Invention, the deep brain stimulation lead has a plurality of electrical contact pads at its distal end and a connector assembly at its proximal end. With respect to catheters utilized to channel microquantities of fluid to a specific location in the brain, the lead includes a thin flexible tube. The proximal ends of these leads connect to external pulse generator and an infusion pump, respectively, generally by means of appropriate extension cables. Specifically with respect to the electrical devices, an electrical signal from the pulse generator is delivered to the target within the brain via the lead. Access to the desired position in the brain is generally accomplished by drilling a hole in the patient's skull or cranium with a cranial drill (commonly referred to as a burr), and coagulating and incising the dura mater, or brain covering.

In accordance with the present invention, and with reference to FIG. 1, the microelectrode 100 is inserted into the central channel of the deep brain stimulation lead 102. The most commonly utilized permanent deep-brain electrodes have an outer diameter of approximately 1.27 mm, and a central axial channel. The side walls of the center channel houses the wire coils 104 which conduct the stimulating current from a connector plug on one end (proximal end, not shown) to the exposed electrode contact pads 106a–d disposed at the distal tip 108 which is located in the brain matter. The center channel traditionally houses a removable stylet used for making the deep-brain stimulating electrode more rigid during placement. Typically, the electrode is placed into the brain to target and the stylet is then removed. The distal tip is dull-shaped to minimize brain trauma as it is being advanced to target. In the present invention, the deep brain stimulation lead is modified slightly in that the distal active tip of the lead is open, whereas it is closed in the traditional embodiment.

As introduced above, the microelectrode 100 consists of a stainless steel wire, approximately 0.27 mm in diameter. This width is approximately the same width as the central channel of the standard deep brain stimulation lead. (Traditional microelectrodes include a polyamide coating as an insulator. If necessary, and as shown in the embodiment illustrated in FIG. 1, the polyamide coating may be removed as the inner surface of the deep brain stimulation lead channel is a sufficient insulator.) The remainder of the microelectrode lead of the present invention may remain similar to those of the prior art, i.e. having an attached tungsten tip 110 with a diameter of 1–3 $\mu$m, and an impedance of 500 to 1000 kOhms at a typical frequency of 1000 Hz. The tungsten tip 110 may be replaced with any suitable alternative high frequency high impedance material which may be sharpened to the same extent that the tungsten material can.

In the case of the traditional microelectrode device, the tip 110 is used as one pole of an electrical circuit, and the distal exposed portion of a stainless steel carrier tube is used as the other pole to form a current loop. In the present invention, the other pole is provided bygone of the permanent DBS electrical contact pads 106a–d, preferably the most distal 106d. Alternatively, a conducting cannula used for inserting the assembly into the proper site in the brain could be used as the other lead.

Single-cell recording is performed and the trajectory of interest is mapped. The signal is filtered, amplified 10,000 fold, and usually recorded for off-line analysis. A simultaneous audio and oscilloscope system can be used to hear and view the data in real time. Whenever neuronal activity is encountered, the electrode location and electrophysiological properties are noted. Once the final depth of the target is determined by MER, the final DBS lead is slid down to the physiologic target and the microelectrode is withdrawn, similar to the withdrawal of a stylet.

Macrostimulation is then performed, as usual, as a final confirmation of the target. This method minimizes the number of trajectories required to determine the optimal final electrode position, and thus possibly minimizes the risk of complication. In addition, it facilitates the use of MER and may yield a more optimal final location and better clinical results.

There has thus been set forth a novel combination of single-cell recording and deep-brain stimulating lead implantation, which minimizes the number of microelectrode trajectories and thereby the possibility of complication. Although a preferred embodiment has been set forth specifically, it is to be noted that other variations and-equivalent embodiments which employ the channel inside the hollow portion of the permanent DBS lead to refine the final placement of the permanent electrode or microcatheter are within the scope of this invention as claimed.

I claim:

1. A combination microelectrode recording device and deep brain stimulation implant for use in function neurosurgery, comprising:

a deep brain stimulation implant which comprises an elongate tubular structure having a first proximal end and a second distal end and an inner channel defined by an elongate cylindrical sidewall which extends the entire length of the tubular structure, said inner channel terminating at openings at both the proximal and distal ends of the elongate structure, said elongate tubular structure further comprising an insulating material;

said deep brain stimulation implant including at least one electrically conducting wire lead extending within the elongate cylindrical sidewall such that the inner channel surface is electrically insulated from said at least one wire lead, said at least one wire lead terminating at two exterior surface conduction pads, one of which is disposed on the exterior surface of the elongate tubular structure adjacent to the proximal end, and the other conduction pad being disposed disposed on the exterior surface of the elongate tubular structure adjacent to the distal end;

a microelectrode recording lead selectively axially translateably disposed within said inner channel of said deep brain stimulation implant such that said microelectrode recording lead may be selectively advanced or retracted through said inner channel; and said microelectrode recording lead having an elongate structure with a first proximal end and a second distal end, comprising an electrically conductive material and having a high frequency high impedence material disposed at the distal tip thereof.

2. The combination microelectrode recording device and deep brain stimulation implant as set forth in claim 1, wherein the insulating material of the deep brain stimulation implant comprises an elastomeric material.

3. The combination microelectrode recording device and deep brain stimulation implant as set forth in claim 1, wherein the at least one wire lead disposed in the deep brain stimulation implant is helically wound within said elongate sidewall, extending around the inner channel.

4. The combination microelectrode recording device and deep brain stimulation implant as set forth in claim 1, wherein said microelectrode recording lead includes an insulating sheath surrounding at least a portion thereof.

5. The combination microelectrode recording device and deep brain stimulation implant as set forth in claim 1, wherein said high frequency high impedence material of said tip of said microelectrode recording lead is tungsten.

* * * * *